US00PP27769P3

(12) United States Plant Patent
Miyazaki

(10) Patent No.: US PP27,769 P3
(45) Date of Patent: Mar. 7, 2017

(54) ***LOBELIA* PLANT NAMED 'SUNLOBE TOREPIN'**

(50) Latin Name: *Lobelia erinus*
Varietal Denomination: Sunlobe Torepin

(71) Applicant: Kiyoshi Miyazaki, Shiga (JP)

(72) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 42 days.

(21) Appl. No.: 14/545,749

(22) Filed: Jun. 15, 2015

(65) Prior Publication Data

US 2016/0366808 P1 Dec. 15, 2016

(51) Int. Cl.
*A01H 5/02* (2006.01)

(52) U.S. Cl.
USPC ..... Plt./451

(58) Field of Classification Search
USPC ..... Plt./451
See application file for complete search history.

*Primary Examiner* — Keith Robinson
(74) *Attorney, Agent, or Firm* — C. A. Whealy

(57) ABSTRACT

A new and distinct cultivar of *Lobelia* plant named 'Sunlobe Torepin', characterized by its outwardly spreading plant habit; vigorous growth habit; freely branching habit; dense and bushy plant form; freely flowering habit; relatively large violet pink-colored flowers; and good garden performance.

1 Drawing Sheet

Botanical designation: *Lobelia erinus.*
Cultivar denomination: 'SUNLOBE TOREPIN'.

BACKGROUND OF THE INVENTION

The present invention relates to a new and distinct cultivar of *Lobelia* plant, botanically known as *Lobelia erinus* and hereinafter referred to by the name 'Sunlobe Torepin'.

The new *Lobelia* plant is a product of a planned breeding program conducted by the Inventor in Higashiomi, Shiga, Japan. The objective of the breeding program is to create new outwardly spreading, freely-branching and bushy Lobelia plants with large attractive flowers and good garden performance.

The new *Lobelia* plant originated from a cross-pollination made by the Inventor in May, 2010 of a proprietary selection of *Lobelia erinus* identified as code number 10Lob31A-1, not patented, as the female, or seed, parent with a proprietary selection of *Lobelia erinus* identified as code number 10Lob31A-2, not patented, as the male, or pollen, parent. The new *Lobelia* plant was discovered and selected by the Inventor as a single flowering plant within the progeny of the stated cross-pollination in a controlled greenhouse environment in Higashiomi, Shiga, Japan in June, 2011.

Asexual reproduction of the *Lobelia* plant by vegetative cuttings in Higashiomi, Shiga, Japan since April, 2012 has shown that the unique features of this new *Lobelia* plant are stable and reproduced true to type in successive generations.

SUMMARY OF THE INVENTION

Plants of the new *Lobelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunlobe Torepin'. These characteristics in combination distinguish 'Sunlobe Torepin' as a new and distinct *Lobelia* plant:

1. Outwardly spreading plant habit.
2. Vigorous growth habit.
3. Freely branching habit; dense and bushy plant form.
4. Freely flowering habit.
5. Relatively large violet pink-colored flowers.
6. Good garden performance.

Plants of the new *Lobelia* differ primarily from plants of the parent selections in the following characteristics:

1. Plants of the new *Lobelia* are more freely branching than plants of the parent selections.
2. Plants of the new *Lobelia* have shorter internodes than plants of the parent selections.

Plants of the new *Lobelia* can be compared to plants of *Lobelia erinus* 'Lobantis', disclosed in U.S. Plant Pat. No. 18,198. In side-by-side comparisons conducted in Higashiomi, Shiga, Japan, plants of the new *Lobelia* differed from plants of 'Lobantis' in the following characteristics:

1. Plants of the new *Lobelia* were more spreading than and not as upright and mounding as plants of 'Lobantis'.
2. Plants of the new *Lobelia* were more vigorous than plants of 'Lobantis'.
3. Plants of the new *Lobelia* had smaller leaves than plants of 'Lobantis'.
4. Plants of the new *Lobelia* had larger flowers than plants of 'Lobantis'.
5. Plants of the new *Lobelia* and 'Lobantis' differed in flower color as plants of 'Lobantis' had light purple-colored flowers.
6. Plants of the new *Lobelia* had longer and thicker peduncles than plants of 'Lobantis'.

BRIEF DESCRIPTION OF THE PHOTOGRAPHS

The accompanying colored photographs illustrate the overall appearance of the new *Lobelia* plant showing the colors as true as it is reasonably possible to obtain in colored reproductions of this type. Colors in the photographs may differ slightly from the color values cited in the detailed botanical description which accurately describe the actual colors of the new *Lobelia* plant.

The photograph at the top of the sheet comprises a side perspective view of a typical flowering plant of 'Sunlobe Torepin' grown in a container.

The photograph at the bottom of the sheet is a close-up view of a typical flowering plant of 'Sunlobe Torepin'.

DETAILED BOTANICAL DESCRIPTION

Plants used for the aforementioned photographs and following description were grown in 15-cm containers in an outdoor nursery in Higashiomi, Shiga, Japan and under cultural practices typical of commercial *Lobelia* production. During the production of the plants, day temperatures averaged 23° C. and night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Lobelia erinus* 'Sunlobe Torepin'.

Parentage:

*Female, or seed, parent*.—Proprietary selection of *Lobelia erinus* identified as code number 10Lob31A-1, not patented.

*Male, or pollen, parent*.—Proprietary selection of *Lobelia erinus* identified as code number 10Lob31A-2, not patented.

Propagation:

*Type cutting*.—Vegetative cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous.

*Rooting habit*.—Freely branching; relatively dense.

Plant description:

*Plant and growth habit*.—Outwardly spreading plant habit; freely branching habit with lateral branches developing at potentially every node; dense and bushy plant habit; vigorous growth habit.

*Plant height*.—About 15 cm.

*Plant width*.—About 54 cm.

*Lateral branch description*.—Length: About 34 cm. Diameter: About 1.9 mm. Internode length: About 2.2 cm. Strength: Strong, flexible. Aspect: Outwardly spreading. Texture: Sparsely pubescent. Color: Close to 138A tinged with close to 165A.

Leaf description:

*Arrangement*.—Alternate, simple; sessile.

*Length*.—About 4 cm.

*Width*.—About 1.5 cm.

*Shape*.—Oblong.

*Apex*.—Obtuse.

*Base*.—Cuneate.

*Margin*.—Serrate.

*Texture, upper and lower surfaces*.—Smooth, glabrous; along the margins, slightly pubescent.

*Venation pattern*.—Pinnate.

*Color*.—Developing leaves, upper surface: Close to 137C. Developing leaves, lower surface: Close to 138B. Fully expanded leaves, upper surface: Close to 137B; venation, close to 138C. Fully expanded leaves, lower surface: Close to 138A; venation, close to 138D.

Flower description:

*Flower arrangement, habit and shape*.—Flowers typically arranged in terminal and lateral racemes; flowers face mostly outwardly to slanting downward; freely flowering habit with about four flowers per inflorescence and about 300 flowers developing per plant; flowers bilabiate with two upper petals and three larger lower petals.

*Fragrance*.—None detected.

*Natural flowering season*.—In Japan, plants of the new *Lobelia* flower continuously from May until October; early flowering habit, plants begin flowering about three to four weeks after planting.

*Flower longevity on the plant*.—Longevity of individual flowers is highly dependent on temperature, flowers typically last about 10 to 14 days on the plant; flowers persistent.

*Inflorescence length*.—About 8.2 cm.

*Inflorescence diameter*.—About 7.7 cm.

*Flower length*.—About 2.3 cm.

*Flower diameter*.—About 2.75 cm.

*Flower tube length*.—About 1.2 cm.

*Flower tube diameter*.—About 5.6 mm.

*Flower buds*.—Length: About 1.5 cm. Diameter: About 5.3 mm. Shape: Club-shaped. Color: Towards the apex, close to 70A; towards the base, close to 145D.

*Petals*.—Arrangement: Single whorl of five petals fused towards the base; two upper petals and three larger lower petals. Upper petals: Length, beyond throat: About 8.4 mm. Width: About 3 mm. Shape: Spatulate. Apex: Obtuse. Margin: Entire. Texture, upper and lower surfaces: Smooth, glabrous. Lower petals: Length, beyond throat: About 1.4 cm. Width: About 9.7 mm. Shape: Elliptic to cordate. Apex: Rounded to retuse. Margin: Entire. Texture, upper and lower surfaces: Smooth, glabrous. Color, upper petals: When opening, upper and lower surfaces: Close to N81B. Fully opened, upper and lower surfaces: Close to N81D; color becoming closer to 76B to 76C with development. Color, lower petals: When opening, upper surface: Close to N82B; towards the base, close to N82C. When opening, lower surface: Close to N82D; towards the base, close to 84D. Fully opened, upper surface: Close to N81D; color becoming closer to 76B to 76C with development. Fully opened, lower surface: Close to N82D; towards the base, close to 84D; color becoming closer to 76B to 76C with development. Color, throat, upper and lower petals: Close to 76D, spots, close to N78A; nectar guides, close to N144B. Color, tube, upper petals: Close to 75A. Color, tube, lower petals: Close to N78C; towards the base, close to NN155C

*Sepals*.—Arrangement: Single whorl of five sepals, fused at the base; star-shaped calyx. Length: About 7.6 mm. Width: About 1.3 mm. Shape: Lanceolate. Apex: Acute. Margin: Entire. Texture, upper and lower surfaces: Smooth, glabrous. Color: When opening, upper and lower surfaces: Close to 137B.

Fully opened, upper surface: Close to 137B. Fully opened, lower surface: Close to 137C.

*Pedicels*.—Length: About 3.5 cm. Diameter: About 0.6 mm. Strength: Strong, flexible. Texture: Smooth, glabrous. Color: Close to 137B.

*Reproductive organs*.—Stamens: Quantity per flower: Five. Stamen length: About 9.6 mm. Anther size: About 1.2 mm by 2.6 mm. Anther shape: Elliptic. Anther color: Close to 79B. Pollen amount: Moderate. Pollen color: Close to 4D. Pistils: Quantity per flower: One. Pistil length: About 8.8 mm. Stigma shape: Bi-lobate. Stigma color: Close to 79C. Style color: Close to 144D. Ovary color: Close to 144B.

*Fruits and seeds*.—Fruit and seed development have not been observed on plants of the new *Lobelia*.

Disease & pest resistance: Plants of the new *Lobelia* have not been noted to be resistant to pathogens and pests common to *Lobelia* plants.

Garden performance: Plants of the new *Lobelia* have been observed to have good garden performance and to tolerate wind, rain and temperatures ranging from about 5° C. to about 28° C.

It is claimed:

1. A new and distinct *Lobelia* plant named 'Sunlobe Torepin' as illustrated and described.

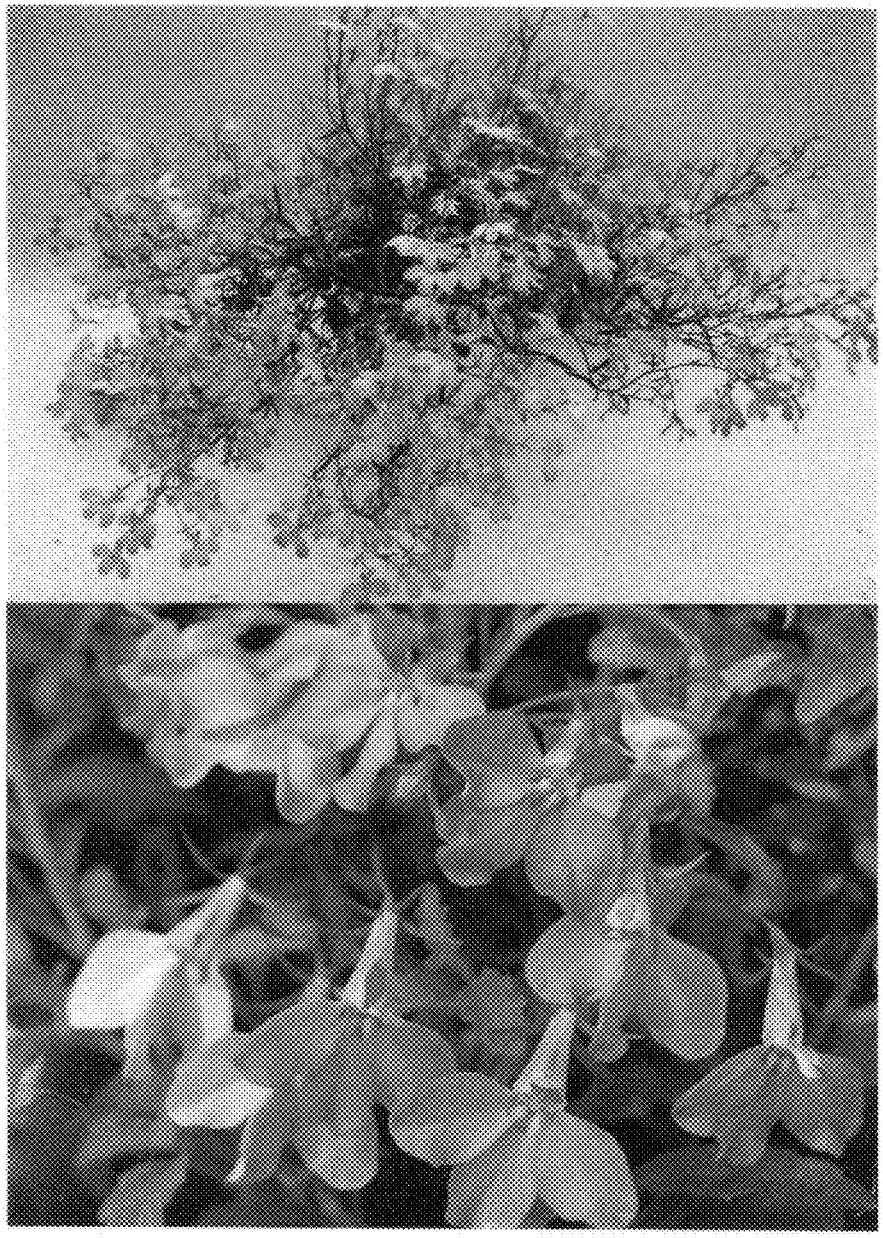

* * * * *